Jan. 31, 1967 R. C. DUNCAN ET AL Re. 26,151

DISPOSABLE DIAPER

Original Filed July 17, 1961 2 Sheets-Sheet 1

INVENTORS

Robert C. Duncan
Norma L. Baker;

BY John V. Gruau

ATTORNEY

DISPOSABLE DIAPER

Original Filed July 17, 1961 2 Sheets-Sheet 2

INVENTORS

Robert C. Duncan
Norma L. Baker,

BY John V. Forman
ATTORNEY

United States Patent Office

Re. 26,151
Reissued Jan. 31, 1967

26,151
DISPOSABLE DIAPER

Robert C. Duncan, Wyoming, and Norma L. Baker, Springfield Township, Hamilton County, Ohio, assignors to The Procter & Gamble Company, Cincinnati, Ohio, a corporation of Ohio Original No. 3,180,335, dated Apr. 27, 1965, Ser. No. 124,422, July 17, 1961. Application for reissue Mar. 21, 1966, Ser. No. 541,055
27 Claims. (Cl. 128—284)

Matter enclosed in heavy brackets [ ] appears in the original patent but forms no part of this reissue specification; matter printed in italics indicates the additions made by reissue.

This invention relates to diapers and more particularly, to paper diapers adapted to be used once and then discarded.

Presently used disposable diapers are, generally speaking, of two types: rectangular or contoured. The rectangular type offers certain advantages in that it combines economy in manufacture and provides a product with a considerable amount of absorptive area and absorbent material in the crotch area of the diaper. However, the bulk of material in the crotch area makes the rectangular diaper difficult to apply to an infant and rather uncomfortable and unattractive in use. In addition, due to the haphazard way in which the diaper is usually applied in most cases, the absorbent material in the crotch area is not utilized to the fullest extent possible. Moreover, its width allows the legs to force the diaper down so that it tends to sag away from the trunk of the body. Thus, the effective absorptive capacity is markedly lower than what one might expect from the amount of absorbent material used in the diaper.

The contoured type of disposable diaper is tailored in an "hour glass" configuration so as to provide an easily applied, neat and attractive product for the use intended. This configuration minimizes the possibility of the legs pushing the diaper away from the trunk. On the other hand, however, this type of diaper is relatively expensive to manufacture because of waste considerations and other problems normally associated with producing an article of irregular lineaments. Furthermore, because some of the absorbent material is removed in cutting the contoured crotch portion, both absorptive area and absorptive capacity of the diaper are considerably reduced.

Both of the aforesaid presently used types have other shortcomings in common. For example, such products, when applied to an infant without the safeguard of an enveloping waterproof panty, are highly susceptible to leakage, wicking and/or seepage of waste matter onto the infant's clothing, thereby soiling the clothes, imparting objectionable odors thereto, making the garments uncomfortable to wear and necessitating the washing thereof. This is true even though some of such products are provided with waterproof outer sheets for the purpose of protecting the clothing from such an occurrence.

Another common fault of the previously discussed products is that the absorptive material of most is prone to become wadded together. This is undesirable from two standpoints: (1) it reduces the absorptive capacity substantially as compared to its initial level and (2) it reduces the surface area available for absorbing liquid, thus limiting the rate at which absorption can take place thereby encouraging further leakage during the extended period of time needed for the liquid to be absorbed.

A further shortcoming of such products is that frequently upon removal of the diaper, pieces of wadding are found adhering to the skin of the infant. This is of considerable annoyance to the party changing the diaper since the pieces must be plucked or washed from the infant and since finding part of the diaper so shredded gives such party the impression that the product is not suitable to perform the function for which it was purchased.

It is an object of the present invention to obviate the above difficulties.

Another object of the present invention is to provide a disposable diaper having sufficient absorptive capacity and which is so constructed as to be easily placed on an infant, neat in appearance, comfortable in use, adapted to protect clothing from being soiled by leakage, wicking and seepage, economically manufactured, and adapted to be disposed of by flushing the absorbent pad down a water closet.

Briefly stated, in accordance with one aspect of this invention, there is provided a disposable diaper comprising a thin flexible back sheet of waterproof material attached to a pad of absorbent material, the combined back sheet and pad being folded into a box pleat configuration by means of a multiplicity of longitudinal folds, the back sheet having oppositely disposed side flap portions adapted to overlie the outermost areas of the uppermost sections of the pleat.

While the specification concludes with claims particularly pointing out and distinctly claiming the subject matter which is regarded as forming the present invention, it is believed that the invention will be better understood from the following description taken in connection with the accompanying drawing, in which:

FIGURE 9 is a perspective view illustrating the way in which the diaper of FIGURE 7 is folded or pleated;

Figure 1:
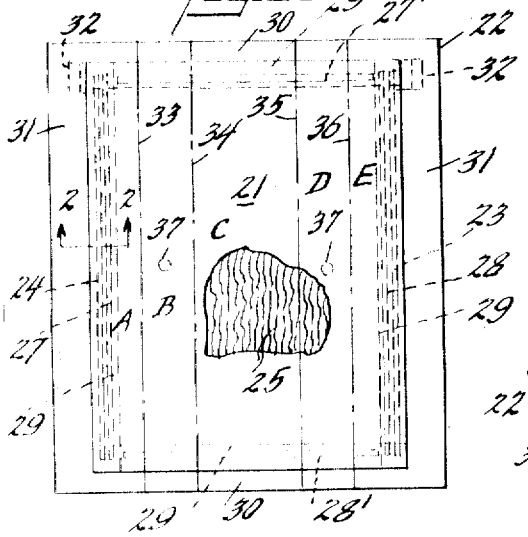
FIGURE 1 is a plan view, partially cut away, of one form of the diaper of this invention prior to folding.

Referring to FIGURE 1, there is shown one embodiment of diaper having an absorbent rectangular pad 21 substantially centrally located on a thin flexible back sheet 22 of waterproof material such as polyethylene having a length and width greater than the corresponding dimension of the pad 21. The pad 21 and back sheet 22 are united, as by adhesive attachment of the contacting surfaces along areas 23 and 24, adjacent the longitudinal side edges of pad 21, to prevent accidental separation and to maintain the position of one relative to the other.

Figure 2:
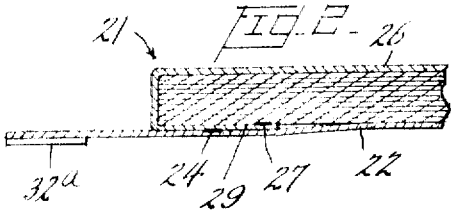
FIGURE 2 is an enlarged fragmentary section taken along line 2—2 of FIGURE 1.

The pad 21, as shown in a preferred form in FIGURE 2, comprises a multiplicity of plies of creped cellulose wadding 25 enclosed on one face and all four edges by a porous, hydrophobic, non-woven fabric top or inner sheet 26. The top sheet 26 is preferably adhesively attached to the bottom face of the plies of wadding 25 and to overlapping portions of itself along the longitudinally extending areas 27 and 28 and laterally extending areas 27' and 28' of the ends and sides 29 of the top sheet 26 which are turned under the wadding 25 and border the bottom face thereof. The adhesive applied along areas 27, 27', 28 and 28' is desirably slowly soluble, if soluble at all, in water so as to obviate the danger of separation of the top sheet 26 from the absorbent wadding 25 in use. A form of binding agent which has been proven adequate is a latex-plasticized polyethylene adhesive such as that sold by the United Shoe Machinery Corp. and identified as Thermogrip #307. Areas 27 and 28, it will be noted, are contiguous to the infolded side edges of top sheet 26, thereby spacing the adhered portions of the top sheet 26 and wadding 25 inwardly from the side edge of the combined unit for a purpose to be described.

The plies of creped cellulose wadding 25 are preferably oriented in a manner placing the machine direction of such plies transverse to the length of the diaper. By such arrangement in a diaper having a configuration such as that shown, the effective capacity of the diaper is increased over pads having the machine direction of wadding 25 oriented so as to extend substantially along the longitudinal dimension of the diaper. This aspect will hereinafter be more fully discussed.

Although the amount of wadding 25 to be used in a diaper of this sort may be varied considerably depending upon the type of performance desired and cost considerations, it has been found desirable to utilize wadding comprising ten plies of tissue having a basis weight (air dry) of 13–15 pounds per ream of 3000 square feet before creping. Preferably, in order to maximize the advantages of orienting the machine direction of the plies transversely of the length of the diaper, the plies of wadding 25 should have about a 60%, or greater, crepe—the percent crepe being equal to one hundred times the quotient of the reduction in length caused by the creping of a piece of tissue divided by the length of the piece of tissue in uncreped form. Wadding 25 of course, is the controlling factor in determining the size of pad 21 since pad 21 will be substantially identical in dimension. In this connection, wadding 25 which is adapted for ready disposal by flushing down a water closet, and which has sufficient capacity for diaper purposes may have a weight of approximately 25 grams and be approximately 12½" wide and 16" long.

The top [shet] *sheet* 26 may be any compliant, soft-feeling, porous, hydrophobic paper or non-woven fabric web. An example of a non-woven fabric sheet which has been found to function well on diapers of this invention is one which comprises 1.5 to 3 denier rayon and contains approximately 20–35% thermoplastic binder (as, for example, copolymers of an ester of acrylic acid such as is sold by the Rohm & Haas Company and identified as B–15), and having a weight of about 15–19 grams per square yard. For best results in processing such a sheet, surfactants should be minimal in the binder emulsion and avoided in the final bath. With wadding 25 dimensioned as set forth above (i.e., 12½" wide by 16" long), an economically and functionally sized top sheet 26 may measure approximately 14½" wide by about 18" long.

Flexible waterproof back sheet 22 desirably comprises a .001" thick low density, opaque polyethylene web which is preferably larger than the corresponding dimensions of the pad 21 by about 1" to about 3" in length and by about 2" to about 4" in width. When so dimensioned, portions of the back sheet 22 extend beyond the perimetric limits of the pad 21, resulting in oppositely disposed end panel extensions 30 and side panel extensions or flaps 31. Good results have been obtained with end panels 30 measuring approximately 1" in width and preferably the side flaps 31 are each approximately 1½" to 1¾" wide, a range which obviates the possibility of the flap slipping outwardly from its proper position in use and of the flaps extending so far inwardly as to detrimentally offset the operation of the diaper as a whole. The purpose or function of the end panels 30 and side flaps 31 will be understood from the discussion following the structural description of the diaper of this invention.

As indicated previously, the pad 21 and back sheet 22 are adhesively united along areas 23 and 24. With the structure above described, it will be realized that it would be undesirable to flush the waterproof back sheet 22 down a water closet along with the pad 21. As a consequence, the bond between the pad 21 and the sheet 22 should be strong in shear but permit the united pad and back sheet to be easily severable by peeling one from the other. One adhesive which has been used and found to be exemplary of the type contemplated for use in uniting the pad 21 with back sheet 22 is a plasticized polyethylene adhesive such as that sold by National Starch and Chemical Corporation and identified as National Starch Resyn #34–3000. This type of bonding agent is applied to the pad as a ⅛" wide stripe at a temperature of approximately 250° F. and cools raipdly to a temperature of approximately 110°–140° F. at which time the pad and back sheet are pressed together. Thereafter, the bond is formed and the adhesive solidified in less than two seconds.

As illustrated in FIGURES 1, 2, 4, and 5 a fastening means such as pressure sensitive tape fasteners 32 may be provided on the side of the sheet 22 opposite to that united with pad 21. The fasteners 32 each comprise a strip of pressure sensitive tape divided into two areas 32a and 32b, each extending the full length of the strip. Area 32b has a release tab 32c covering and held by the film of adhesive on that area, the tab having an easily gripped free side extending outwardly which is formed by folding release tab 32c back on itself along its longitudinal axis. The fasteners 32 are located on the underside of the back sheet 22, one on each side flap 31 adjacent a top corner of pad 21 (as shown in FIGURE 1), being attached by means of the adhesive on the area 32a of each of the fasteners.

With the components of the diaper in the assembled form of FIGURE 1, longitudinal folds are made along fold lines 33, 34, 35 and 36, thereby dividing the pad 21 and the underlying parts of back sheet 22 into five sections [A, B, C, D and E], *i.e. central section C, a pair of oppositely disposed inside sections B and D, and a pair of terminal sections A and E.* It will be noted that section C is centrally disposed and occupies approximately one-third of the width of pad 21, while sections A, B, D and E are approximately equal and each has a width of about one-sixth of the transverse dimension of pad 21. Sections A and B are juxtaposed and connected with one [edge] *side* of section C and sections D and E are also side-by-side, being connected with the other [edge] *side* of section C. Sections A and E, the outermost of the five divisions, each have *an outer side edge which comprises a free edge of the pad 21 and have* extending therefrom one of the side panel extensions or flaps 31.

At a time immediately before folding along the lines 33–36, a spot 37 of adhesive is placed substantially on the lateral axis of sections B and D at points which preferably lie between about one-tenth to about five-eighths of the width of said sections from fold lines 33 and 37, respectively. Alternatively, such adhesive spot could be placed on section C at positions spaced and located so as to provide attachment to sections B and D at the points above described when the diaper is folded. The primary function of the spots 37 is to hold the crotch area diaper in the folded configuration at least until the diaper is secured to the infant, after which such means is helpful but not essential in maintaining the structure. While other means could be utilized in performing this function (e.g., staples, stitching, etc.) the spots 37 comprise the preferred mode. One type of adhesive suitable for use in this connection is a plasticized polyethylene adhesive such as was described above with respect to the bonding of pad 21 to the back sheet 22. *No adhesive is applied to the ends of the section to maintain the folded configuration and, hence, the folds are unsecured, and therefore the pad 21 freely laterally spreadable, at the ends.*

Figure 3:
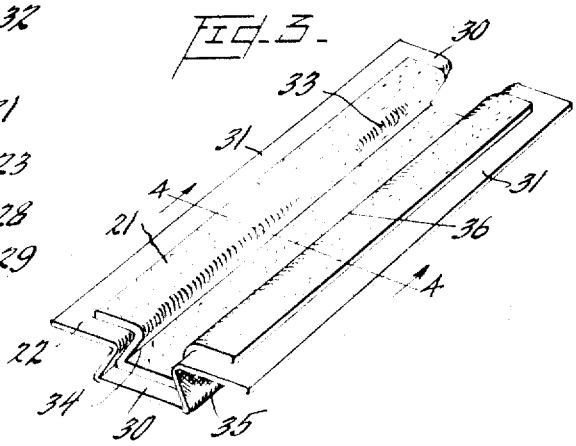
FIGURE 3 is a perspective view illustrating the way in which the diaper of FIGURE 1 is folded or pleated.

The diaper is preliminarily formed as shown in FIG. 3, folding sections B and D inwardly along fold lines 34 and 35 respectively *in non-overlapping relationship* so that the portions of top sheet 26 of these setcions contact that of *the top face of* section C and the adhesive spot 37 unites the parts of the top sheet 26 which directly underlie and overlay each of said spots in folded condition, and folding sections A and E outwardly along lines 33 and 36 respectively whereby sections A and B lie back-to-back and *the inner sides thereof* are juxtaposed to similarly oriented sections D and E. When thus formed, the various sections of this embodiment of diaper assume a box pleated configuration held in position by the spots 37 of adhesive. The opposed folds along fold lines 33 and 36 (*which define and locate the integral connections of the inner sides of the inside sections B and D with the inner sides of terminal sections A and E, respectively,*) are substantially parallel to and adjacent the longitudinally extending axis of the device and may be spaced from one another preferably by a distance of about one-eighth to about one-half of an inch.

Figure 4:
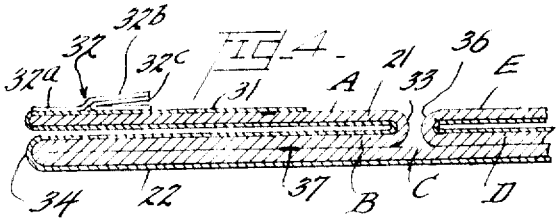
FIGURE 4 is an enlarged fragmentary section taken along line 4—4 of FIGURE 3 following the completion of the folding and gluing operations.

Next, each of the side flaps 31 is folded inwardly over the portion of top sheet 26 on the section A or E, from which it extends as illustrated in FIGURE 4. The diaper is now in condition to be packaged and sold as a commercial product. In this connection, the pleated structure described permits the product to be conveniently packed as a compact unit, the diaper merely being folded laterally across the center of the diaper, whereas disposable diapers of the prior art have been packaged in unfolded form.

Figure 5:
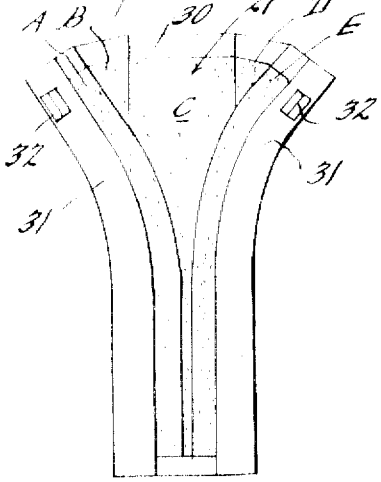
FIGURE 5 is a plan view of the folded diaper of FIGURES 1–4 with one end fanned outwardly in preparation for application to an infant.

In use, the diaper is laid on a surface in preparation for the placement of the baby thereon and one end "fanned" out. The waist-underlying ends of outermost *or terminal* sections A and E (those on the end of the diaper having the fasteners 32 mounted thereon) are grasped and are pulled in opposite directions, laterally and outwardly, so as to spread that end of the diaper with the superposed side flaps 31 remaining in the same relative position with respect to sections A and E, substantially as shown in FIGURE 5. The infant is then positioned on the waist-underlying end of the diaper with the buttocks centered laterally thereon and spaced slightly from the longitudinal center in the direction of the fanned out end. In this position, it will be noted that the other end of the diaper will extend downwardly, between the legs of the baby. Next, the downwardly extending end of the diaper is brought up between the infant's legs to a position contiguous to the front of the child's waist, and that end fanned out as was done with the waist-underlying end. The last steps placed the central area of the diaper in the baby's crotch region, with the adhesive spot 37 maintaining the pleated structure in that area. The diaper is then secured to the child by placing the corners of the waist portion of the abdomen-covering end as far around the infant's waist as they will go and bringing the corners of the underlying end into overlapping relationship with the first mentioned corners so that the diaper snugly encircles the child's waist. The overlapping corners are fixed in such positions by means of safety pins or by means of the pressure sensitive tape fasteners 32. In the latter case, the corners are held in position manually and the release tabs 32b grasped and pulled from engagement with the tape 32a and the tape 32a simultaneously engaged with the subjacent corners in much the same way that adhesive bandages are applied over a wound. The diaper, when applied to the infant, assumes the form depicted in FIGURE 6—a highly efficient, economically made, attractive, disposable diaper.

It will be noted that by virtue of the pleat maintained in the central part of the diaper in use, the entire crotch portion (including the diaper side edges) is adapted to fit more closely adjacent the trunk of the child than would be possible if the diaper was to be applied in straight rectangular form. Such close proximity is extremely important since not only the appearance but also the efficacy of the product is thereby affected. In this connection, it is recognized that whereas inwardly turned waterproof panels such as side flaps 31 might be adapted, when used in conjunction with many other forms of diaper, merely to prevent dripping and "wicking" directly from the pad, the functions of the flaps in the present invention have been considerably broadened by including (in addition to the above-mentioned dripping and "wicking" protection) the prevention of leakage around, rather than through the diaper and also by improved reception and retention of solid wastes.

Figure 6:
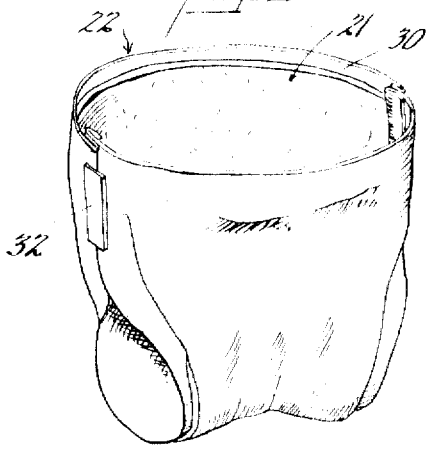
FIGURE 6 is a perspective view showing the form which the diaper assumes in use.

After the diaper is applied to the infant, the diaper's pleated construction and the child's natural movements cause the diaper crotch area to become bent in the central portion thereof as shown in FIGURE 6. In this condition, the side edges of the pleat in the crotch area become turned downwardly slightly, causing the compliant side flaps 31 in that area to assume a position contiguous to the infant's legs along an area of the inner, rear and front portions of the thighs adjacent the junction thereof with the child's torso. In this position the flaps are very effective in preventing or minimizing leakage from the diaper, thereby giving the absorbent material within the diaper sufficient time to absorb the liquid wastes to thus utilize, as fully as possible, the absorptive power of the diaper and simultaneously prevent soiling of garments which come into contact with the baby. Since the diaper configuration is originally rectangular, the maximum amount of absorptive area and absorbent material is most economically maintained in the crotch area—an important factor with respect to disposable diapers and especially significant where the diaper is provided with an effective means of retaining the fluids in contact with the material.

Figure 11:
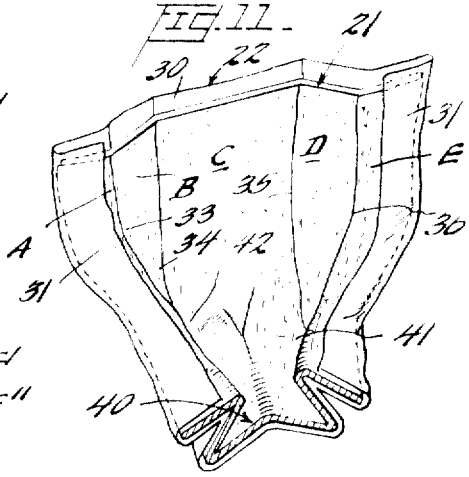
FIGURE 11 is a fragmentary perspective view of the interior of a diaper of this invention fanned out and bent so as to illustrate the approximate diaper configuration in use.

When the diaper becomes bent in the crotch portion as described above, the folds along fold lines 33 and 36 at the crotch portion become slightly further separated from each other and from the underlying section C, forming, as shown in FIGURE 11, an open channel-like arrangement 40 between portions of sections B, C and D in the crotch area and also forming open troughs 41 and 42 in the transitional areas of the diaper intermediate the crotch portion and the fully unfolded areas spaced from the crotch portion at either end of the diaper. The channel-like arrangement 40 and the troughs 41 and 42 are an aid in directing fluid wastes toward the ends of the diaper and in addition serve as receptacles to retain and prevent the undesirable spread of solid wastes to other areas of the diaper. These advantageous functions are achieved in large measure because of the structure and fit of the diaper in the crotch area and the improved retention characteristics presented by the pleat-side flap combination.

As mentioned previously, it is decidedly advantageous to orient the plies of wadding 25 so as to place the machine direction of the plies transverse to the length of the diaper. In this position, the ridges of the creping run substantially parallel with the length of the diaper. It is a fact that moisture being absorbed by a sheet of uncreped paper will be absorbed at a rate substantially equal in all directions on the sheet—for example, a drop of water placed thereon will wet a substantially circular area of the paper. However, a drop of water applied to the surface of a creped paper does not result in a wet area having a substantially circular configuration as viewed in plan, rather it produces an elliptically shaped moistened area. The major axis of the ellipse parallels the ridges of creping, or in other words, is normal to the machine direction of the sheet. If the creped paper were stretched to an uncreped condition, of course, it would be discovered that the wet area of this uncreped sheet, too, is substantially circular.

Thus, it will be seen that if there is any advantage derived purely from the orientation of a pad with respect to the crepe ridges, such seems to be small at best. Consequently, for a given area of wadding in an absorptive device, all other things being equal, it will not generally matter which way the machine direction of the wadding extends since the absorbent capacity will be the same. For this reason it would normally be expected to be a moot question as to whether the crotch area of the diaper should have the ridges of the crepe in the longitudinal or in the transverse direction of the diapers of this invention since the absorbency is about the same in either case.

It will be realized, of course, that because of the rapidity of an infant's discharge while urinating, any directional advantage in preventing side leakage due merely to the orientation of the sheet will have substantially no effect. This would be especially true in a diaper of common construction and merely utilizing waterproof side flaps in order to prevent dripping or wicking from the side margins of the diaper, since this form of diaper would tend to prevent leakage through the side and promote lengthwise flow to unsaturated portions of the diaper regardless of the direction of creping.

Despite the findings with respect to other forms of diapers, when the creped wadding of the diaper of this invention, i.e., one which has the pleated configuration previously described, is oriented with the machine direction of the plies substantially transverse its length, a substantial increase is noted in the in-use absorptive capacity of the diaper as compared with devices of the same configuration having the machine direction of the wadding extending lengthwise. The in-use absorptive capacity of a diaper system may be defined as the capacity of the diaper, when applied to an infant, in absorbing liquids without objectionable wetting of the infant's clothing, bed linens, etc.

Although the underlying reason for the increase in in-use capacity is not precisely understood, it is believed that the principal factor involved is the in-use stresses upon the creped plies of this diaper which are greater in the direction transverse the diaper length than they are along the length of the diaper. By placing the machine direction of the plies in the direction of the greater stresses, the greater length of the plies in the machine direction plus the "give" permitted by the creping makes the pad 21 more resistant to tearing and consequently results in fewer failures. Although it would not seem, at first blush, to be important to restrict tearing of the pad 21 or to be possible to increase the in-use capacity by such means, this does appear to be the case. The mechanism of the enhancement is believed to reside in minimizing the amount of "balling" or gathering together or agglomeration of the wadding—an effect engendered by the rupture or failure of the plies in use. As previously pointed out, agglomeration of the wadding reduces the absorbent capacity of the diaper substantially, and in addition, reduces the surface area of the wadding thereby limiting unduly the rate at which further absorption can take place. The upshot of the matter is that this novel diaper construction more effectively maintains the capacity and rate of absorption of the wadding than other forms of construction (utilizing pads oriented in a different way).

Placement of the pad 21 so that the machine direction of the plies 25 of wadding extend transversely of the length is also an aid in reducing the shredding of the plies 25 which tend to adhere to the skin of the infants in disposable diapers of the prior art. Such shredding is particularly prevalent where the ends of the pad 21 are not enclosed by turned-under portions of a top sheet as found in the embodiment of this invention previously described.

The end panel extensions have been found to be particularly desirable for use with the present invention since diapers having a relatively high-in-use absorptive capacity saturate a more widespread area of the diaper, presenting a greater possibility of "wicking" from the waist-covering portions of the diaper to clothes touching the diaper in this region. With end panel extensions having the preferred width of approximately one inch, ample protection is economically afforded against this form of leakage without sacrificing comfort or appearance.

Along these same lines, i.e., because of the relatively high in-use absorptive capacity and the consequent more widespread area of saturation of the device of this invention, a greater portion of the skin of the child is contiguous to the wetted areas of the diaper. Such a condition while deemed proper from the standpoint of capacity is considered one of the contributing factors which might promote the development of a diaper rash on the infant and for this reason should be taken into account in designing the device. It is the function of the porous hydrophobic top sheet 26 to permit moisture to readily pass into the layers of creped wadding 25 but to resist the return flow thereof from the underlying absorbent material to thus act much the same as a one-way valve. In this way, the infant's skin is insulated insofar as is possible, from the moisture absorbed by the diaper and thus will be less likely to develop a rash. The top sheet may comprise any material which is not easily wetted and preferably has a porosity such as that of a web made in accordance with the specifications of denier, etc., previously set forth. In this connection, as used herein the word hydrophobic is intended to generally describe the materials which, when a drop of water is placed on an unsupported surface thereof, will not permit the drop to "wet out" in less than five seconds.

Following use, the diaper is removed from the infant in the usual manner following the disengagement of the overlaping corners at the child's waist. Then the diaper is held vertically over the bowl portion of a water closet, permitting entrapped solids to drop into the bowl, with the fingers of one hand grasping the upper end of the pad 21 and those of the other hand grasping the upper end panel extension 30. Next, the back sheet 22 is briskly pulled downwardly and away from the pad 21, thereby peeling the two apart along the adhesively united areas 23 and 24, and the back sheet 22 disposed of by placing the same in a wastepaper basket. Following separation, the pad 21 is dipped several times in the water in the water closet bowl until a major portion of the plies of creped wadding 25 is repulped and loosely deposited in the water. Then the water closet is flushed (while the remaining portion of the pad 21 is still held) until most of the repulped material has been carried away, at which point the remaining portion may be dropped into the water for similar disposal.

The way in which the plies of wadding 25 and the top sheet 26 of pad 21 are held together along the longitudinally extending areas 27 and 28 and the relative position of these areas 27 and 28 with respect to the areas 23 and 24 along which the pad 21 is attached to back sheet 22 are significant from the standpoint of easy separation of the pad from the back sheet. It will be recalled that the form of bond interconnecting the pad 21 and the back sheet 22 was previously described as being relatively strong in shear (to assure that the shear stresses in use do not cause separation) and weak in peel (to aid in disposing of the pad). Thus, an advantage is derived if the back sheet 22 may be peeled from the pad 21. If the glue areas 27 and 28 were located outwardly of the glue areas 23 and 24, the inturned side edges of top sheet 26 would open outwardly during the separation step, substantially paralleling the back sheet 22, necessitating a shear failure of the bond at the areas 23 and 24—involving greater effort and being much less reliable in trouble-free separation. With the glue areas in the preferred positions, however, the inwardly turned side edges of top sheet 26 are maintained contiguous to the plies of wadding 25 so as to permit the pad 21 and back sheet 22 to be readily separated by failure in peel.

In the embodiment of FIGURES 7–10, portions of the device similar to that already described in connection with the embodiment of FIGURES 1–6 will be assigned corresponding reference numerals and no further explanation thereof presented. As shown, this embodiment has extending entirely across the pad 21, in the central portion thereof, an absorptice insert 38 of creped cellulose wadding. The insert 38 may be "sandwiched" between the plies of wadding 15 having its machine direction transverse the length of the diaper. The purpose of the insert is to provide additional absorbent material in the most critical zone—the crotch area of the diaper—to give the diaper an added measure of protection where the diaproper service is likely to be needed for an extended period of time or where the urinary output of the child is exceptionally high. While the additional material comprising the insert 38 reinforces the absorptive capacity of the diaper, the surface area available for absorbing liquids remains substantially the same and for this reason the advantages previously pointed out with respect to the pleats and side flaps and the pleats and pad orientation of this invention come into play to more fully exploit the capacity of insert 38—from the standpoint of maintaining the available surface area and preventing leakage until the liquids have had time to be absorbed.

The modification of FIGURES 7–10 also has means thereon to fasten the ends of inwardly folded edges of side flaps 31 in position over the face of pad 21. Such means is shown to be dots 39 of adhesive placed at each end of the outermost sections A and E at points to be covered by the flaps 31. It is important that the flaps 31 be unsecured in the crotch area so as to permit them to properly function as previously discussed. While the dot 39 of adhesive may be of the same type as is used along areas 23 and 24 in securing the pad 21 to the back sheet 22, it has been found that an adhesive wax is entirely satisfactory. Such a product is sold by Glyco Chemicals, a division of Charles L. Huisking & Co., Inc., being identified as Flexowax C–Light, and is merely heated to 110° to 120° F. and applied. This type of adhesive solidifies and bonds without compression in aproximately one-half second when small amounts are used. By so fastening the flaps 31, the possibility of the flaps unfolding during the application of the diaper to the infant is diminished.

The method of disposal of the diaper of FIGURES 7–10 is substantially identical with that previously described, since the flaps of this embodiment are easily broken loose from adhesive attachment to top sheet 26 at dots 39.

Figure 7:
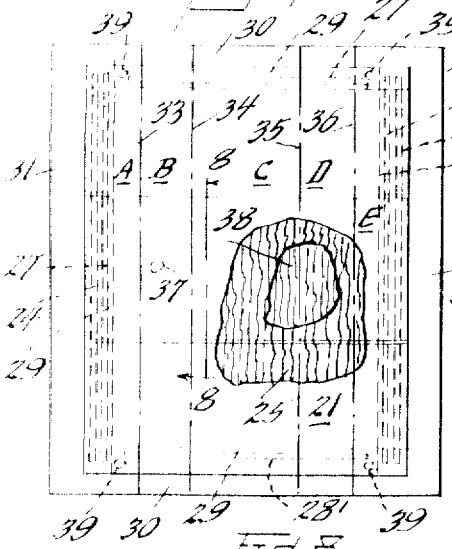
FIGURE 7 is a plan view, partially cut away, of a modified form of the diaper of this invention prior to folding.
Figure 8:
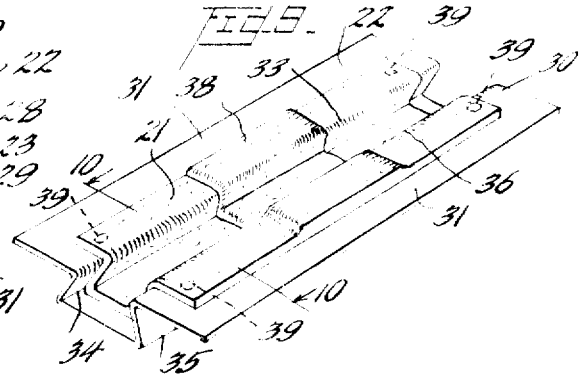
FIGURE 8 is an enlarged fragmentary section taken along line 8—8 of the embodiment shown in FIGURE 7.
Figure 10:
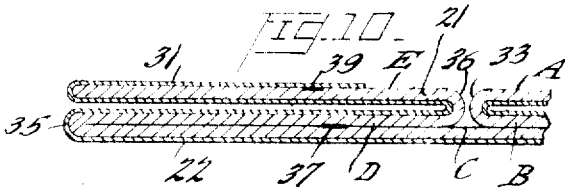
FIGURE 10 is an enlarged fragmentary section taken along line 10—10 of FIGURE 9 following the completion of the folding and gluing operations.
Figure 5:
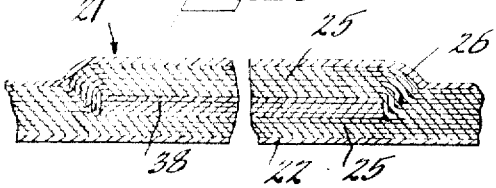
Figure 12:
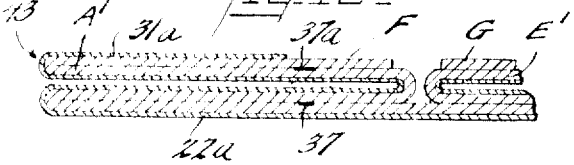
FIGURE 12 is an enlarged fragmentary section, similar to FIGURES 4 and 10, showing an alternative method of folding the diaper.
Figure 13:
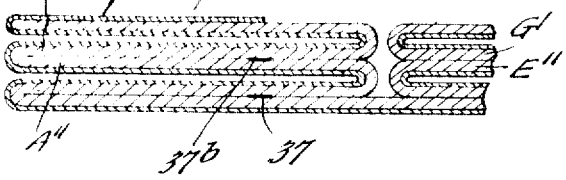
FIGURE 13 is an enlarged fragmentary section of another embodiment, illustrating a further method of folding the diaper.

As illustrated in FIGURES 12 and 13, the diaper of this invention may be folded in other ways so as to gain the advantages previously outlined. In the embodiment of FIGURE 12, for example, additional absorbent sections F and G are provided in supraposed relationship with sections A′ and E′. Such an arrangement is substantially similar to the above described diapers with the principal exception that extra folds are made in the pad and an additional adhesive spot 37a is provided in a position equivalent to that of spot 37 with respect to the innermost folds so as to secure each of sections F and G to underlying sections A′ and E′ respectively *whereby to form a pair of double-layered terminal sections A′–F and E′–G*. The flaps 31a of the waterproof back sheet 22a are folded inwardly over sections F and G in the same manner and operate in the same way as flaps 31 of the embodiments previously described. Other structural details may be arranged somewhat the same as shown in FIGURES 1 and 7. For example, the absorbent pad may be attached to back sheet 22a by means of an adhesive stripe applied lengthwise contiguous to fold 43 on the dorsal side of section A′ and a counterpart thereof on the other side (not shown) of the diaper of FIGURE 12. Thus, this construction teaches the feasibility of preparing side flap equipped diapers having a modified form of box pleat from diapers having absorbent pads of a greater actual lateral dimension than the width of the back sheet. This is possible since the effective width of the pad of this embodiment (i.e., the combined width of all the sections of the pad intermediate the outer sides of sections A′ and E′) is smaller than that of the back sheet 22a so as to provide the oppositely disposed side flaps 31a.

The structure of the diaper embodiment of FIGURE 13 involves twice as many folds as those of FIGURES 1 and 7 resulting in another form for the box pleat forming a part of this invention. Aside from the increased number of sections folded together, *a pair of which is located intermediate to and connecting each terminal section and the inside section underlying it*, an the additional adhesive spots 37b utilized in fastening sections F′ and G′ to sections A″ and E″, respectively, the structure of this embodiment, too, may be substantially similar to those of FIGURES 1 and 7.

Many modifications of the above invention may be used and it is not intended to hereby limit it to the particular embodiments shown or described. The terms used in describing the invention are used in their descriptive sense and not as terms of limitation, it being intended that all equivalents thereof be included within the scope of the appended claims.

What is claimed is:

1. A disposable diaper comprising a thin flexible back sheet of waterproof material having an absorbent pad superposed thereon, said back sheet having a width exceeding that of said pad so as to provide oppositely disposed side flaps, the pad and underlying back sheet being formed into a box pleat configuration by means of a multiplicity of longitudinal folds defining diaper sections comprising the pleat, the side flaps being folded inwardly so as to enclose the side edges of said pad and overlie the outermost areas of the uppermost sections of the pleat while leaving the innermost areas thereof uncovered so as to expose portions of said absorbent pad, whereby when applied to an infant said diaper substantially eliminates waste fluid leakage around the leg conforming portions thereof.

2. The disposable diaper of claim 1 in which said pad comprises a multiplicity of plies of creped cellulose wadding having an absorbent insert therein extending transversely across substantially the full width of said pad.

3. The disposable diaper of claim 1 in which said pad is formed from a multiplicity of plies of creped cellulose wadding covered on one face and on all edges thereof by a porous, hydrophobic top sheet.

4. The disposable diaper of claim 2 in which said plies of said pad are covered on one face and on all edges thereof with a porous hydrophobic top sheet.

5. A disposable diaper comprising a thin flexible back sheet of waterproof material having superposed thereon a pad of absorbent material, said pad and back sheet being formed into a box pleat configuration by means of a multiplicity of longitudinal folds, said pad comprising a plurality of plies of creped cellulose wadding, said pad being oriented with the ridges of the creping of the plies of creped cellulose wadding therein extending in a direction substantially parallel to the longitudinal dimension of the diaper.

6. The disposable diaper of claim 5 in which said pad includes a centrally located absorbent insert extending across substantially the full width of said pad.

7. The disposable diaper of claim 5 in which said plies of creped cellulose wadding are covered on one face and on all edges by a porous, hydrophobic top sheet.

8. The disposable diaper of claim 6 in which said pad is covered on one face and on all edges by a porous, hydrophobic top sheet.

9. A disposable diaper comprising a thin flexible back sheet of waterproof material having superposed thereon a pad of absorbent cellulosic material, said back sheet having a width exceeding that of said pad so as to provide oppositely disposed complaint side flaps, the pad an underlying back sheet being formed into a box pleat configuration by means of a multiplicity of longitudinal folds defining diaper sections comprising the pleat, the side flaps being folded inwardly so as to enclose the side edges of said pad and overlie the outermost areas of the uppermost sections of the pleat, said pad comprising a plurality of plies of creped cellulose wadding having the ridges of the creping thereof extending substantially parallel to the lengthwise dimension of said diaper.

10. The disposable diaper of claim 9 in which said pad has centrally located therein an absorbent insert extending substantially across the full width of the said pad.

11. The disposable diaper of claim 9 in which said pad is covered on one face and on all edges thereof with a porous, hydrophobic top sheet.

12. The disposable diaper of claim 10 in which said pad is covered on one face and on all edges thereof by a porous, hydrophobic top sheet.

13. A disposable diaper comprising a thin flexible back sheet of waterproof material having a pad of absorbent cellulosic material attached thereto, the side edges of said back sheet being spaced outwardly of the corresponding side edges of said pad thus forming laterally extending side flaps adapted to be folded inwardly over the side margins of said pad, said diaper being formed into a box pleated structure by means of four longitudinal folds, said pad comprising a multiplicity of plies of creped cellulose wadding having the ridges of the creping thereof extending transverse to the width of said diaper and a centrally located absorbent insert extending substantially across the full width of said pad.

14. A disposable diaper comprising an absorbent cellulosic pad fastened to a waterproof back sheet, said pad comprising a multiplicity of plies of creped cellulose wadding with an absorbent insert substantially centrally located therein which extends across the full width of said pad and a top sheet extending across the face and enclosing all edges of said plies, said top sheet comprising a porous, hydrophobic material, the width of said pad being substantially less than the width of said back sheet whereby laterally extending side flaps are formed, said side flaps being folded inwardly over the pad to a position enclosing the side edges of said pad and overlying marginal areas of said pad adjacent its side edges, the ridges of the creping of the plies of creped cellulose wadding in said pad extending along the length of said pad, said diaper being formed into a box pleated structure by means of four longitudinal folds.

15. A disposable diaper of substantially rectangular lineaments comprising a thin flexible back sheet of waterproof material with a pad of absorbent cellulosic material attached thereto, the side edges of said back sheet being spaced outwardly of the corresponding side edges of said pad, said pad and underlying back sheet being formed into a box pleat configuration in at least the crotch area thereof by means of at least two inwardly turned and two outwardly turned folds defining diaper sections comprising the pleat, said inwardly turned folds being located on opposite sides of the longitudinal center of said diaper and oriented to fold towards one another over the top of said pad, the location of each inwardly turned fold being intermediate that of an outwardly turned fold and said longitudinal center of the diaper in flat condition, the said side edges of said pad in the crotch area being positioned to substantially align with the said inwardly turned folds of the pleated structure, the side portions of said back sheet which are spaced outwardly of said pad being folded inwardly so as to enclose the side edges of said pad and overlie the outermost areas of the uppermost sections of the pleat while leaving the innermost areas thereof uncovered so as to expose portions of said absorbent pad.

16. A disposable diaper of substantially rectangular lineaments comprising a thin flexible back sheet of waterproof material having attached thereto a pad of absorbent material, the end edges of said pad being spaced inwardly of the corresponding end edges of said back sheet, said pad and underlying back sheet being formed into a box pleated structure by means of a multiplicity of longitudinal folds, said pad comprising a plurality of plies of creped cellulose wadding, said pad being oriented with the ridges of the creping of the plies of creped cellulose wadding therein extending in a direction substantially parallel to the longitudinal dimension of the diaper.

17. A disposable diaper of substantially rectangular lineaments comprising a thin flexible back sheet of waterproof material having attached thereto a pad of absorbent cellulosic material, the side and end edges of said pad being spaced inwardly of the corresponding side and end edges of said back sheet, said pad and underlying back sheet being formed into a box pleated structure by means of four longitudinal folds, the side portions of said back sheet which are spaced outwardly of said pad being folded inwardly so as to enclose the side edges of said pad and overlie marginal areas of said pad adjacent the side edges thereof, said pad comprising a multiplicity of plies of creped cellulose wadding having the ridges of the creping thereof extending substantially parallel to the lengthwise dimension of said diaper.

18. A disposable diaper of substantially rectangular configuration comprising a thin flexible back sheet of waterproof material having attached thereto a pad of absorbent celluosic material, the side and end edges of said pad being spaced inwardly of the corresponding side and end edges of said back sheet, said diaper being formed into a box pleated structure by means of a multiplicity of longitudinal folds defining diaper sections comprising the pleat, the side portions of said back sheet which are spaced outwardly of said pad being folded inwardly so as to enclose the side edges of said pad and overlie the outermost areas of the uppermost sections of the pleat, said pad comprising a multiplicity of plies of creped cellulose wadding having the ridges of the creping thereof extending substantially parallel to the lengthwise dimension of said diaper, said pad being covered on one face and all edges with a porous, hydrophobic top sheet.

19. A disposable diaper of substantially rectangular configuration comprising a thin flexible back sheet of waterproof material having attached thereto a pad of absorbent cellulosic material, the side and end edges of said pad being spaced inwardly of the corresponding side and end edges of said back sheet, said pad and underlying back sheet being formed into a box pleated structure by means of four longitudinal folds, the side portions of said back sheet spaced outwardly of said pad being folded inwardly so as to enclose the side edges of said pad and overlie marginal areas of said pad adjacent the side edges thereof, said pad comprising a multiplicity of plies of creped cellulose wadding having the ridges of the creping thereof extending substantially parallel to the lengthwise dimension of said diaper, and a centrally located absorbent insert extending substantially across the full width of said pad.

20. A disposable diaper of substantially rectangular configuration comprising a thin flexible back sheet of waterproof material having attached thereto a pad of absorbent cellulosic material, the side and end edges of said pad being spaced inwardly of the corresponding side and end edges of said back sheet, said pad and underlying back sheet being formed into a box pleated structure by means of four longitudinal folds, the side portions of said back sheet spaced outwardly of said pad being folded inwardly so as to enclose the side edges of said pad and overlie marginal areas of said pad adjacent the side edges thereof, said pad comprising a multiplicity of plies of creped cellulose wadding having the ridges of the creping thereof extending substantially parallel to the lengthwise dimension of said diaper, said pad being covered on one face and all edges with a porous, hydrophobic top sheet, and a centrally located absorbent insert extending substantially across the full width of said pad.

21. A disposable diaper comprising a thin flexible back sheet of waterproof mateiral having an absorbent pad attached thereto, said back sheet having a width exceeding that of said pad so as to provide oppositely disposed side flaps, said pad and underlying back sheet being formed into a box pleated configuration in at least the crotch region thereof by means of a multiplicity of longitudinally extending folds in such region, said side flaps being folded inwardly so as to enclose the side edges and overlie the side marginal areas of the pad while leaving the innermost areas thereof uncovered so as to expose portions of said absorbent pad, whereby when applied to an infant said diaper substantially eliminates waste fluid leakage around the leg conforming portions thereof.

*22. A disposable diaper comprising a pad formed into a box-pleat configuration by means of a multiplicity of longitudinal folds, said folds being unsecured at the ends of said pad whereby the pad is freely laterally spreadable at said ends, said pad being constructed of a plurality of plies of creped cellulose wadding, said pad being oriented with the ridges of the creping of the plies of creped cellulose wadding therein extending in a direction substantially parallel to the longitudinal dimension of the pad.*

*23. The disposable diaper of claim 22 in which said plies of creped cellulose wadding are covered on one face and on all edges by a porous, hydrophobic top sheet.*

*24. A disposable diaper pad in combination with waterproof means to prevent leakage, wicking and seepage therefrom, said pad being formed into a box-pleat configuration by a multiplicity of longitudinal folds which are unsecured at the ends of said pad whereby the pad is freely laterally spreadable at said ends, said pad being constructed of a plurality of plies of creped cellulose wadding, the ridges of the creping of said plies of creped cellulose wadding extending in a direction substantially parallel to the longitudinal dimension of the pad.*

*25. A disposable diaper comprising a pad formed into a box pleat configuration by means of a multiplicity of longitudinal folds, said folds being unsecured at the ends of said pad whereby the pad is freely laterally spreadable at said ends, said box pleat configuration including a central section, a pair of oppositely disposed inside sections connected to the sides of said central section and folded in non-overlapping relationship with one another over one face of said central section with the inner sides of said inside sections juxtaposed, and a pair of outwardly facing terminal sections overlying said inside sections, each of said terminal sections having an outer side edge which comprises a free edge of said pad, said pad being constructed of a plurality of plies of creped cellulose wadding oriented with the ridges of creping thereof extending in a direction substantially parallel to the longitudinal dimension of the pad.*

*26. The disposable diaper of claim 25 in which the inner side of each terminal section is integrally connected directly to an underlying inside section, said integral connections occurring along fold lines defining the inner sides of said inside and terminal sections.*

*27. The disposable diaper of claim 25 in which at least one pair of additional sections is located intermediate each terminal section and the inside section underlying it and serves to connect the same.*

References Cited by the Examiner

The following references, cited by the Examiner, are of record in the patented file of this patent or the original patent.

UNITED STATES PATENTS

| | | | |
|---|---|---|---|
| 1,971,671 | 8/1934 | Alsop | 128—286 |
| 2,571,577 | 10/1951 | Howard | 128—284 |
| 2,622,051 | 4/1952 | Hermanson et al. | 161—128 |
| 2,788,786 | 4/1957 | Dexter | 128—284 |
| 2,829,647 | 4/1958 | Dexter | 128—284 |
| 2,890,700 | 6/1959 | Lonberg-Holm | 128—284 |
| 2,896,626 | 7/1959 | Voigtman | 128—287 |
| 2,905,176 | 9/1959 | Davidson | 128—284 |
| 3,067,747 | 12/1962 | Wolterding et al. | 128—296 |

FOREIGN PATENTS

| | | |
|---|---|---|
| 522,749 | 3/1956 | Canada. |
| 794,500 | 5/1958 | Great Britain. |

ROBERT E. MORGAN, *Acting Primary Examiner.*

C. F. ROSENBAUM, *Assistant Examiner.*